US 6,572,745 B2
(12) United States Patent
Rappin et al.

(10) Patent No.: US 6,572,745 B2
(45) Date of Patent: *Jun. 3, 2003

(54) ELECTROCHEMICAL SENSOR AND METHOD THEREOF

(75) Inventors: Craig Rappin, Long Grove, IL (US); Kiamars Hajizadeh, Lincolnshire, IL (US); Kelly Mills, McHenry, IL (US)

(73) Assignee: Virotek, L.L.C., Buffalo Grove, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/017,751

(22) Filed: Dec. 7, 2001

(65) Prior Publication Data

US 2002/0157947 A1 Oct. 31, 2002

Related U.S. Application Data

(63) Continuation-in-part of application No. 09/820,372, filed on Mar. 23, 2001.

(51) Int. Cl.$^7$ ............................................. G01N 27/327
(52) U.S. Cl. ........................ 204/403.14; 204/403.01; 204/416; 204/403.02
(58) Field of Search ...................... 204/403.01–403.15, 204/416, 431, 433, 434, 412

(56) References Cited

U.S. PATENT DOCUMENTS

| | | | |
|---|---|---|---|
| 3,838,033 A | 9/1974 | Mindt et al. ............... | 205/195 |
| 3,925,183 A | 12/1975 | Oswin et al. .............. | 204/195 |
| 3,979,274 A | 9/1976 | Newman ................... | 435/180 |
| 4,005,002 A | 1/1977 | Racine et al. ............. | 204/195 |
| 4,053,381 A | 10/1977 | Hamblen et al. .......... | 204/195 |
| 4,137,495 A | 1/1979 | Brown ....................... | 324/30 |
| 4,169,779 A | 10/1979 | Tataria et al. ............. | 204/195 |
| 4,217,196 A | 8/1980 | Huch ........................ | 204/195 |
| 4,224,125 A | 9/1980 | Nakamura et al. ........ | 204/195 B |
| 4,225,410 A | 9/1980 | Pace ......................... | 204/195 |
| 4,239,471 A | 12/1980 | Swaroop .................... | 425/144 |
| 4,254,083 A | 3/1981 | Columbus .................. | 422/55 |
| 4,321,123 A | 3/1982 | Nakamura et al. ........ | 204/195 |
| 4,356,074 A | 10/1982 | Johnson .................... | 204/195 P |
| 4,376,689 A | 3/1983 | Nakamura et al. ........ | 204/195 B |
| 4,392,933 A | 7/1983 | Nakamura et al. ........ | 204/403 |
| 4,407,959 A | 10/1983 | Tsuji et al. ................ | 435/288 |

(List continued on next page.)

FOREIGN PATENT DOCUMENTS

| | | |
|---|---|---|
| EP | 0121385 A1 | 3/1983 |
| EP | 0 078 590 A1 | 5/1983 |
| EP | 0 078 636 B1 | 5/1983 |

(List continued on next page.)

OTHER PUBLICATIONS

International Search Report for PCT/US02/08703 mailed Dec. 6, 2002.
Laboratory Techniques in Electroanalytical Chemistry; pp. 51–61 and 124 (Kissinger and Heineman, eds. 1984) no month available.

*Primary Examiner*—Nam Nguyen
*Assistant Examiner*—Alex Noguerola
(74) *Attorney, Agent, or Firm*—Wallenstein & Wagner, Ltd.

(57) ABSTRACT

A sensor is provided for the determination of various concentrations of one or more components within a fluid sample. The sensor includes an injection molded body, at least two electrodes, an enzyme, and if desired, an electron transfer mediator. The body includes a reaction zone for receiving a fluid sample. The electrodes are at least partially embedded within the plastic body and extend into the reaction zone. Also contained within the reaction zone is an enzyme capable of catalyzing a reaction involving a compound within the fluid sample. Additionally, the sensor incorporates fill detection which activates a meter, attached to the sensor, for measuring the electrochemical changes occurring in the reaction zone.

62 Claims, 6 Drawing Sheets

U.S. PATENT DOCUMENTS

| | | | |
|---|---|---|---|
| 4,413,407 A | 11/1983 | Columbus | 29/825 |
| 4,418,148 A | 11/1983 | Oberhardt | 435/180 |
| 4,420,564 A | 12/1983 | Tsuji et al. | 204/403 |
| 4,431,507 A | 2/1984 | Nankai et al. | 204/403 |
| 4,432,366 A * | 2/1984 | Margules | 600/345 |
| 4,472,131 A | 9/1984 | Ryder | 425/548 |
| 4,473,457 A | 9/1984 | Columbus | 204/416 |
| 4,474,183 A * | 10/1984 | Yano et al. | 600/353 |
| 4,490,216 A | 12/1984 | McConnell | 204/1 |
| 4,502,660 A | 3/1985 | Luther et al. | 249/144 |
| 4,502,938 A | 3/1985 | Covington et al. | 204/412 |
| 4,543,326 A | 9/1985 | Miyashita et al. | 435/15 |
| 4,545,382 A | 10/1985 | Higgins et al. | 128/635 |
| 4,579,643 A | 4/1986 | Mase et al. | 204/424 |
| 4,591,550 A | 5/1986 | Hafeman et al. | 435/4 |
| 4,634,366 A | 1/1987 | Brun et al. | 425/526 |
| 4,654,197 A | 3/1987 | Lilja et al. | 204/403 |
| 4,655,901 A | 4/1987 | Mase et al. | 204/426 |
| 4,682,602 A | 7/1987 | Prohaska | 128/635 |
| 4,711,245 A | 12/1987 | Higgins et al. | 128/635 |
| 4,717,113 A | 1/1988 | Martin | 249/63 |
| 4,758,323 A | 7/1988 | Davis et al. | 204/403 |
| 4,765,585 A | 8/1988 | Wieder | 249/64 |
| 4,768,747 A | 9/1988 | Williams et al. | 249/63 |
| 4,796,014 A | 1/1989 | Chia | 340/573 |
| 4,810,633 A | 3/1989 | Bauer et al. | 435/25 |
| 4,810,658 A | 3/1989 | Shanks et al. | 436/172 |
| 4,820,399 A | 4/1989 | Senda et al. | 204/403 |
| 4,820,636 A | 4/1989 | Hill et al. | 435/14 |
| 4,830,959 A | 5/1989 | McNeil et al. | 435/7 |
| 4,832,307 A | 5/1989 | Watanabe et al. | 249/63 |
| 4,836,904 A | 6/1989 | Armstrong et al. | 204/294 |
| 4,894,137 A | 1/1990 | Takizawa et al. | 204/403 |
| 4,897,173 A | 1/1990 | Nankai et al. | 204/403 |
| 4,900,405 A | 2/1990 | Otagawa et al. | 401/153.16 |
| 4,900,424 A | 2/1990 | Birth et al. | 204/409 |
| 4,927,516 A | 5/1990 | Yamaguchi et al. | 204/403 |
| 4,935,105 A | 6/1990 | Churchouse | 204/153.12 |
| 4,935,106 A | 6/1990 | Liston et al. | 204/403 |
| 4,938,860 A | 7/1990 | Wogoman | 204/403 |
| 4,948,727 A | 8/1990 | Cass et al. | 435/18 |
| 4,952,300 A | 8/1990 | Diamond | 204/406 |
| 4,959,005 A | 9/1990 | Sorensen | 425/577 |
| 4,959,305 A | 9/1990 | Woodrum | 435/7 |
| 4,970,145 A | 11/1990 | Bennetto et al. | 204/403 |
| 4,978,503 A | 12/1990 | Shanks et al. | 422/58 |
| 4,995,402 A | 2/1991 | Smith et al. | 128/771 |
| 4,999,582 A | 3/1991 | Parks et al. | 324/438 |
| 5,015,426 A | 5/1991 | Maus et al. | 264/40.5 |
| 5,030,310 A | 7/1991 | Wogoman | 156/252 |
| 5,040,963 A | 8/1991 | Beck et al. | 425/130 |
| 5,049,487 A | 9/1991 | Phillips et al. | 435/4 |
| 5,120,420 A | 6/1992 | Nankai et al. | 204/403 |
| 5,122,244 A | 6/1992 | Hoenes et al. | 204/153.12 |
| 5,128,015 A | 7/1992 | Szuminsky et al. | 204/403 |
| 5,139,714 A | 8/1992 | Hettinga | 264/45.1 |
| 5,140,393 A | 8/1992 | Hijikihigawa et al. | 357/25 |
| 5,141,868 A | 8/1992 | Shanks et al. | 435/288 |
| 5,171,689 A | 12/1992 | Kawaguri et al. | 435/290 |
| 5,173,165 A | 12/1992 | Schmid et al. | 204/403 |
| 5,192,415 A | 3/1993 | Yoshioka et al. | 204/403 |
| 5,286,362 A | 2/1994 | Hoenes et al. | 204/403 |
| 5,288,636 A | 2/1994 | Pollmann et al. | 435/288 |
| 5,346,659 A | 9/1994 | Buhler et al. | 264/68 |
| 5,354,447 A | 10/1994 | Uenoyama et al. | 204/403 |
| 5,407,344 A | 4/1995 | Rombalski, Jr. et al. | 425/190 |
| 5,437,999 A | 8/1995 | Diebold et al. | 435/288 |
| 5,508,171 A | 4/1996 | Walling et al. | 205/777.5 |
| 5,509,410 A | 4/1996 | Hill et al. | 128/637 |
| 5,527,173 A | 6/1996 | Miller et al. | 425/126.1 |
| 5,547,555 A | 8/1996 | Schwartz et al. | 204/418 |
| 5,560,939 A | 10/1996 | Nakagawa et al. | 425/139 |
| 5,575,895 A | 11/1996 | Ikeda et al. | 204/403 |
| 5,582,697 A | 12/1996 | Ikeda et al. | |
| 5,593,852 A | 1/1997 | Heller et al. | 435/14 |
| 5,595,771 A | 1/1997 | Foltuz et al. | 425/443 |
| 5,639,672 A | 6/1997 | Burd et al. | 436/525 |
| 5,653,934 A | 8/1997 | Brun, Jr. et al. | 264/334 |
| 5,682,884 A | 11/1997 | Hill et al. | 128/637 |
| 5,695,949 A | 12/1997 | Galen et al. | 435/14 |
| 5,707,662 A | 1/1998 | Bright et al. | 425/547 |
| 5,727,548 A | 3/1998 | Hill et al. | 128/637 |
| 5,736,173 A | 4/1998 | Wright et al. | 425/577 |
| 5,762,770 A | 6/1998 | Pritchard et al. | 204/403 |
| 5,798,031 A | 8/1998 | Charlton et al. | 204/403 |
| 5,820,551 A | 10/1998 | Hill et al. | 600/347 |
| 5,833,824 A * | 11/1998 | Benton | 204/416 |
| RE36,268 E | 8/1999 | Szuminsky et al. | 205/777.5 |
| 5,965,380 A | 10/1999 | Heller et al. | 435/14 |
| 5,985,129 A | 11/1999 | Gough et al. | |
| 5,997,817 A | 12/1999 | Crismore et al. | 422/58 |
| 6,059,946 A | 5/2000 | Yukawa et al. | 204/403 |
| 6,071,251 A | 6/2000 | Cunningham et al. | 600/584 |
| 6,101,791 A | 8/2000 | Louviere | 53/467 |
| 6,110,696 A | 8/2000 | Brown et al. | 435/7.6 |
| 6,117,292 A * | 9/2000 | Ahmad | 204/416 |
| 6,129,823 A * | 10/2000 | Hughes et al. | 204/403.1 |
| 6,143,576 A | 11/2000 | Buechler | 436/518 |
| 6,156,270 A | 12/2000 | Buechler | 422/58 |
| 6,162,611 A | 12/2000 | Heller et al. | 435/14 |
| 6,162,639 A | 12/2000 | Douglas | 435/287.1 |
| 6,175,752 B1 | 1/2001 | Say et al. | 600/345 |
| 6,206,841 B1 | 3/2001 | Cunningham et al. | 600/584 |
| 6,241,862 B1 | 6/2001 | McAleer et al. | 204/403 |
| 6,294,062 B1 | 9/2001 | Buck, Jr. et al. | 204/400 |
| 2001/0050228 A1 | 12/2001 | Jaeger | 204/403 |
| 2002/0002344 A1 | 1/2002 | Douglas et al. | 600/583 |
| 2002/0003087 A1 | 1/2002 | Chih-hui | 204/400 |
| 2002/0029964 A1 | 3/2002 | Matsumoto | 204/403 |
| 2002/0053523 A1 | 5/2002 | Liamos et al. | 205/787 |
| 2002/0092612 A1 | 7/2002 | Davies et al. | 156/292 |

FOREIGN PATENT DOCUMENTS

| | | | |
|---|---|---|---|
| EP | 0080304 A1 | | 6/1983 |
| EP | 0096095 A1 | | 12/1983 |
| EP | 0 125 137 B1 | | 11/1984 |
| EP | 0127958 A2 | | 12/1984 |
| EP | 0136362 A1 | | 4/1985 |
| EP | 0 136 362 B1 | | 4/1985 |
| EP | 0 170 375 A2 | | 2/1986 |
| EP | 0 171 148 A1 | | 2/1986 |
| EP | 0 177 743 B1 | | 4/1986 |
| EP | 0206218 A2 | | 12/1986 |
| EP | 0 230 472 A1 | | 8/1987 |
| EP | 0 230 786 A1 | | 8/1987 |
| EP | 0 241 309 A3 | | 10/1987 |
| EP | 0 255 291 A1 | | 2/1988 |
| EP | 0359831 A1 | | 3/1990 |
| EP | 0 170 375 B1 | | 5/1990 |
| EP | 0400918 A1 | | 12/1990 |
| EP | 0 171 148 B1 | | 4/1991 |
| EP | 0 127 958 B1 | | 3/1992 |
| EP | 0 255 291 B1 | | 6/1992 |
| EP | 0 230 472 B1 | | 1/1993 |
| EP | 0 127 958 B2 | | 4/1996 |
| EP | 0 230 472 B2 | | 12/2000 |
| EP | 1098000 A2 * | | 5/2001 |
| EP | 1 098 000 A2 | | 5/2001 |
| GB | 2154003 | | 8/1985 |
| GB | 2204408 A | | 11/1988 |
| JP | 55-10584 | | 1/1980 |

| | | |
|---|---|---|
| JP | 57-98853 | 6/1982 |
| JP | 59-166852 | 9/1984 |
| JP | 60-173457 | 9/1985 |
| JP | 60-173458 | 9/1985 |
| JP | 60-173459 | 9/1985 |
| JP | 60-211350 | 10/1985 |
| JP | 61-90050 | 5/1986 |
| JP | 61-91558 | 5/1986 |
| JP | 61-294356 | 12/1986 |
| JP | 62/137559 | 6/1987 |
| JP | 62-156553 | 7/1987 |
| JP | 63-3248 | 1/1988 |
| JP | 63-3249 | 1/1988 |
| JP | 63-58149 | 3/1988 |
| JP | 63-128252 | 5/1988 |
| JP | 63-139246 | 6/1988 |
| JP | 63-317757 | 12/1988 |
| JP | 63-317758 | 12/1988 |
| JP | 1-91558 | 4/1989 |
| JP | 1-114746 | 5/1989 |
| JP | 1-114747 | 5/1989 |
| JP | 1-134244 | 5/1989 |
| JP | 1-156658 | 6/1989 |
| WO | WO 86/04926 | 8/1986 |
| WO | WO 86/07632 | 12/1986 |
| WO | WO 88/03270 | 5/1988 |
| WO | WO 89/08713 | 9/1989 |

* cited by examiner

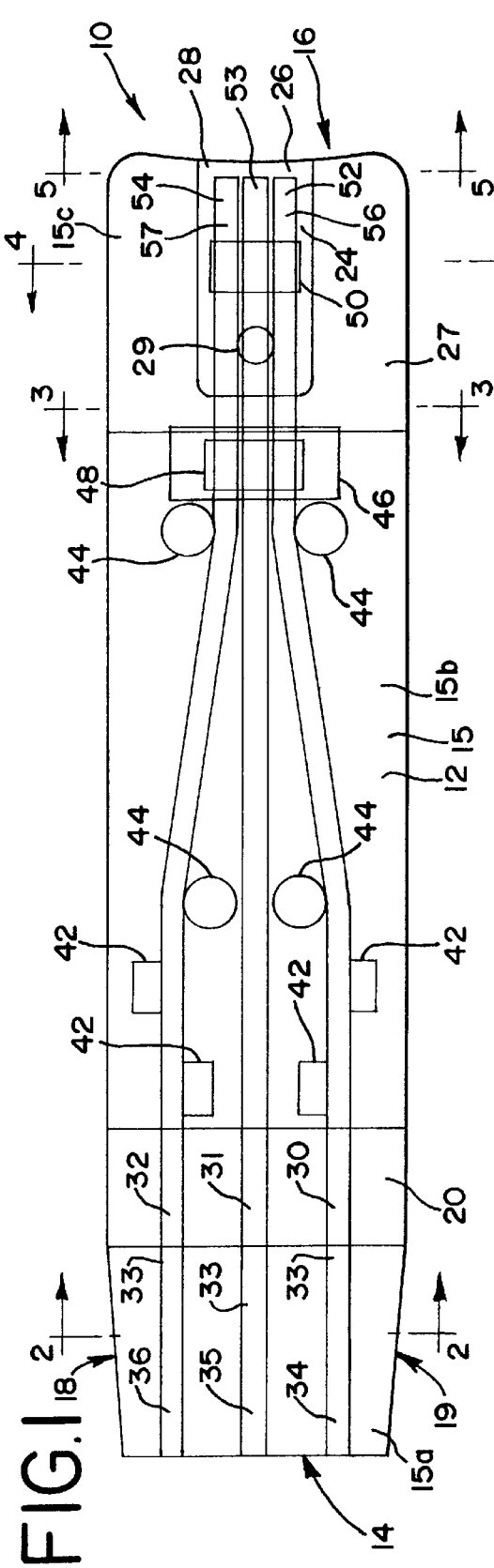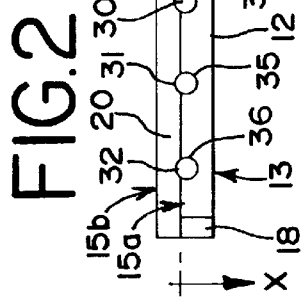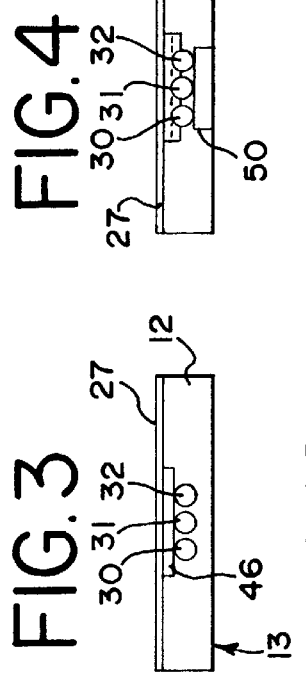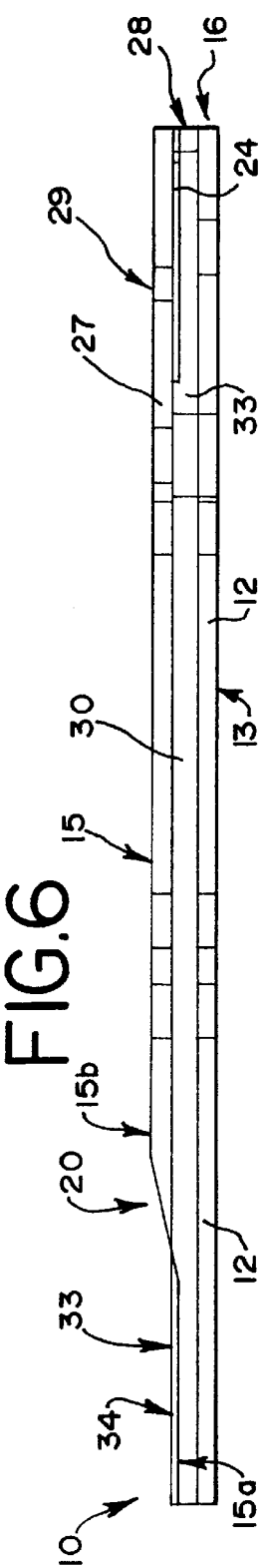

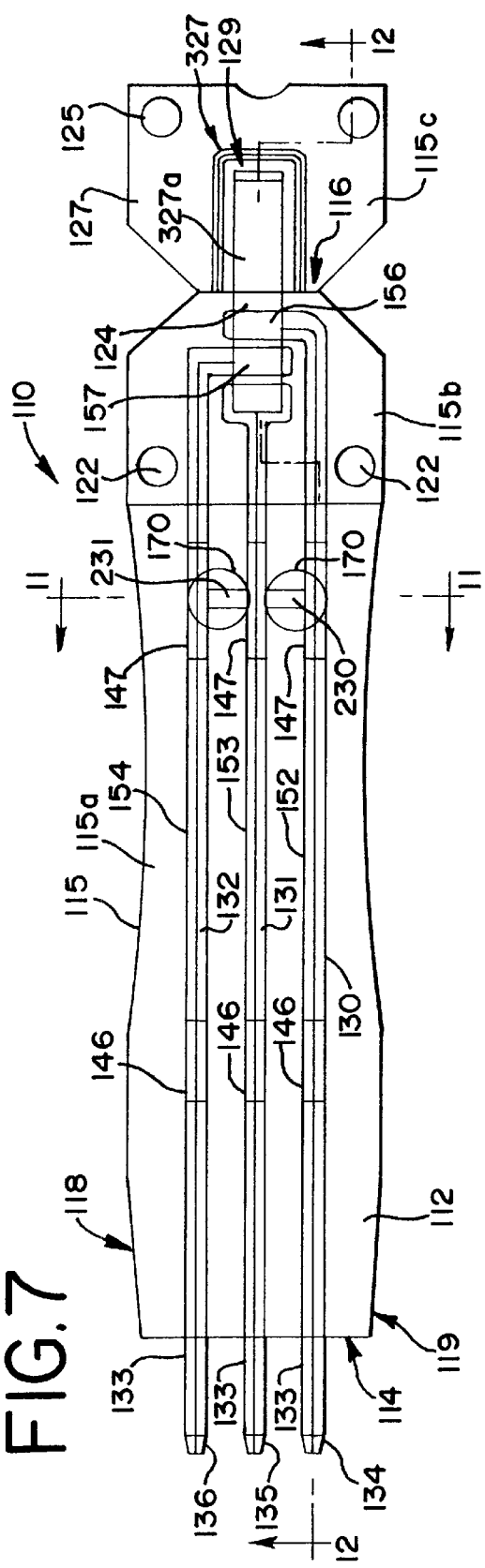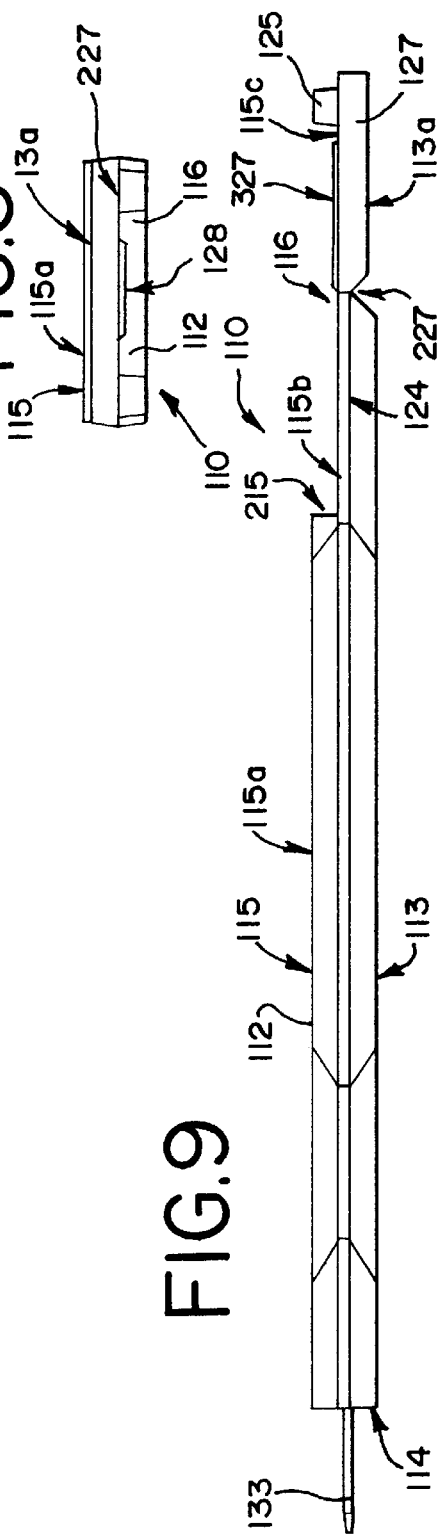

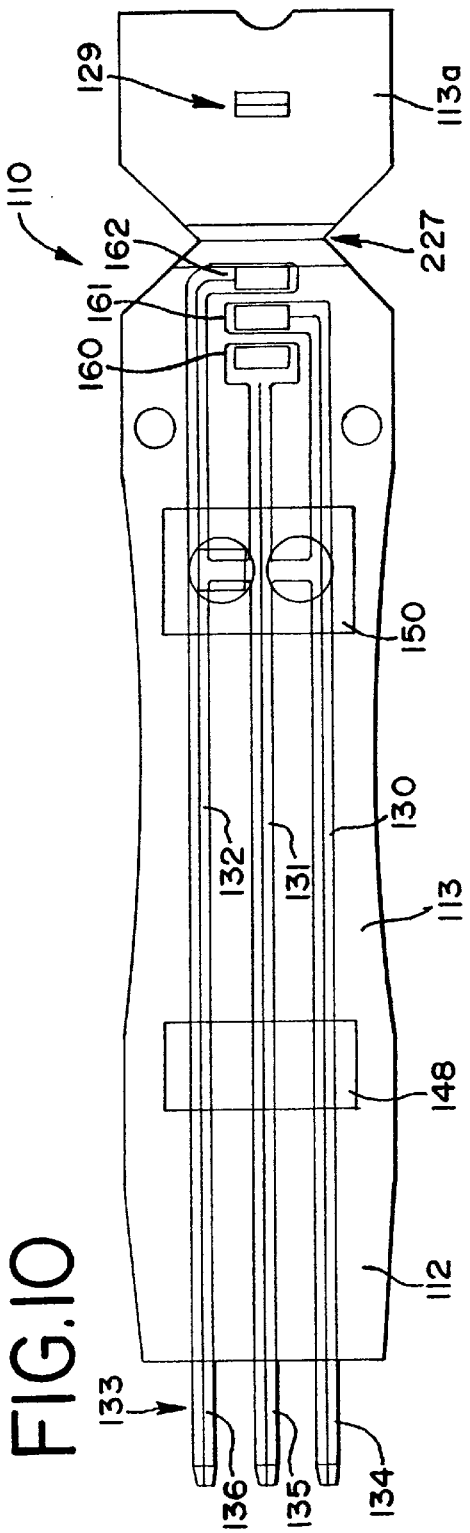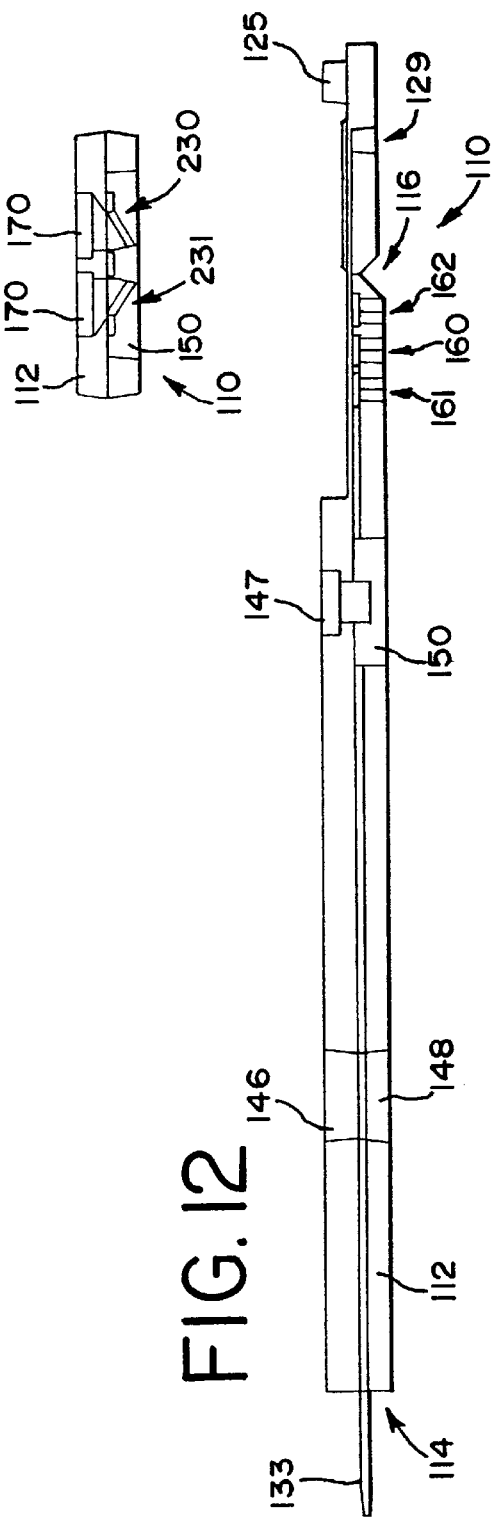

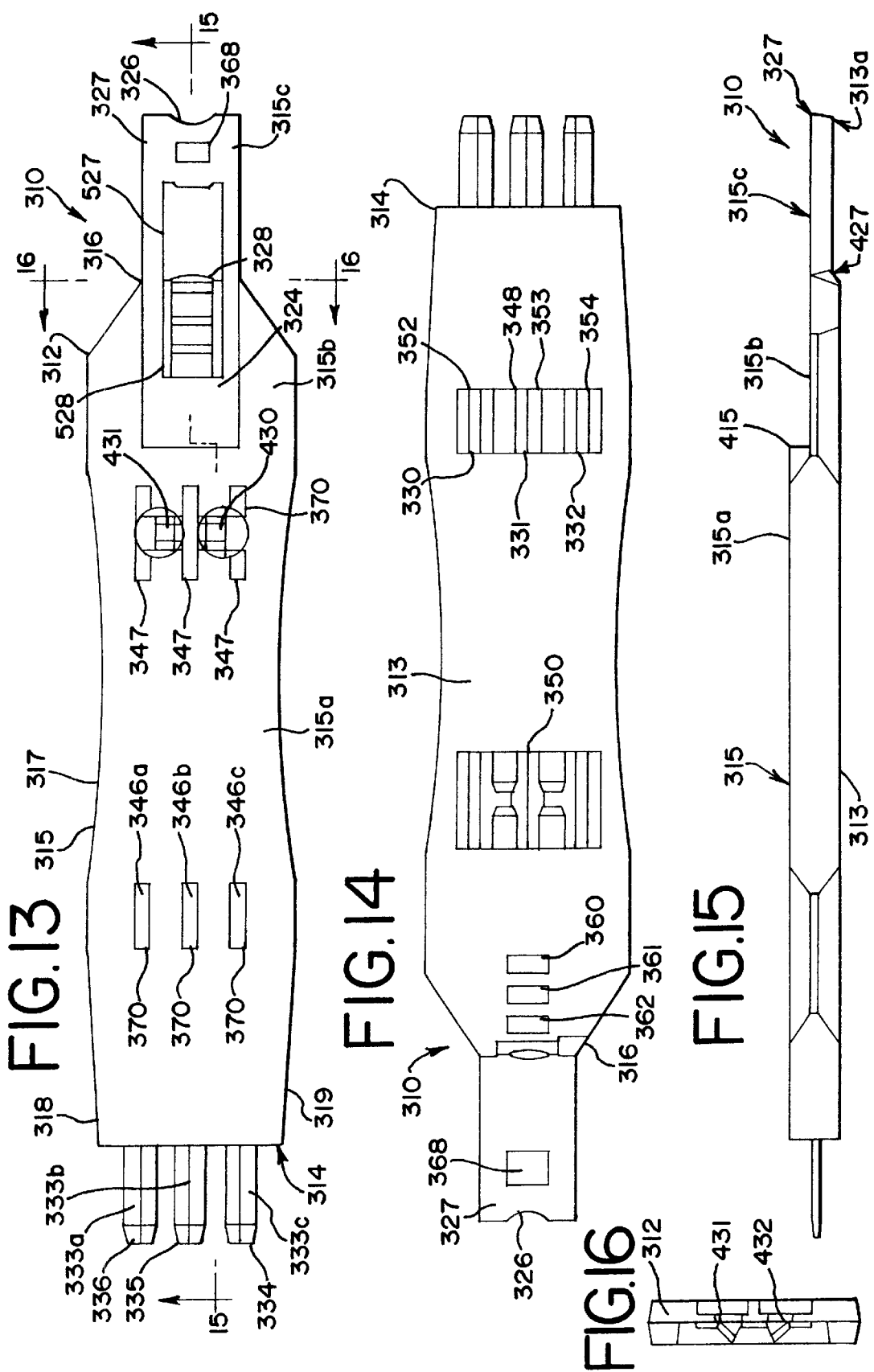

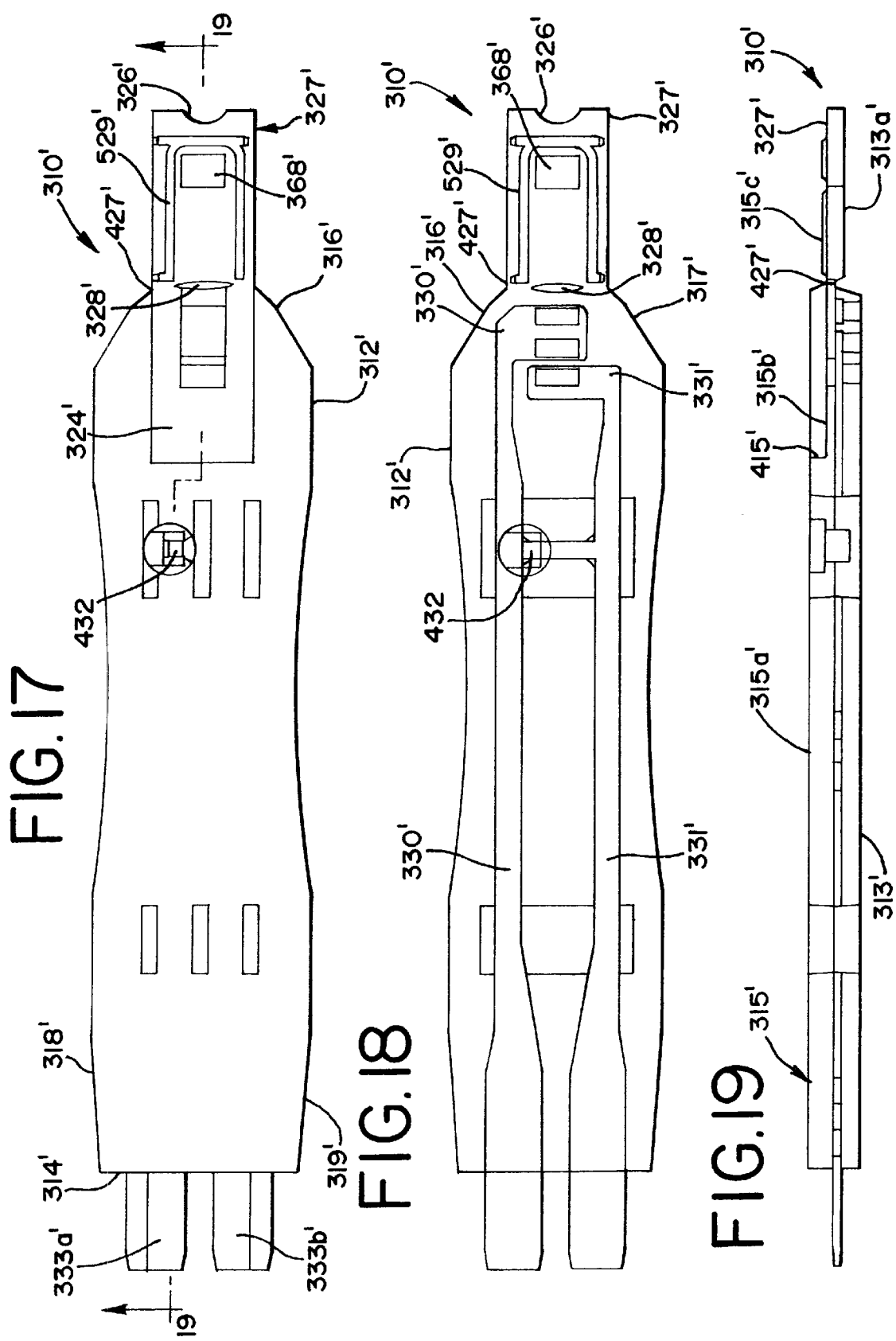

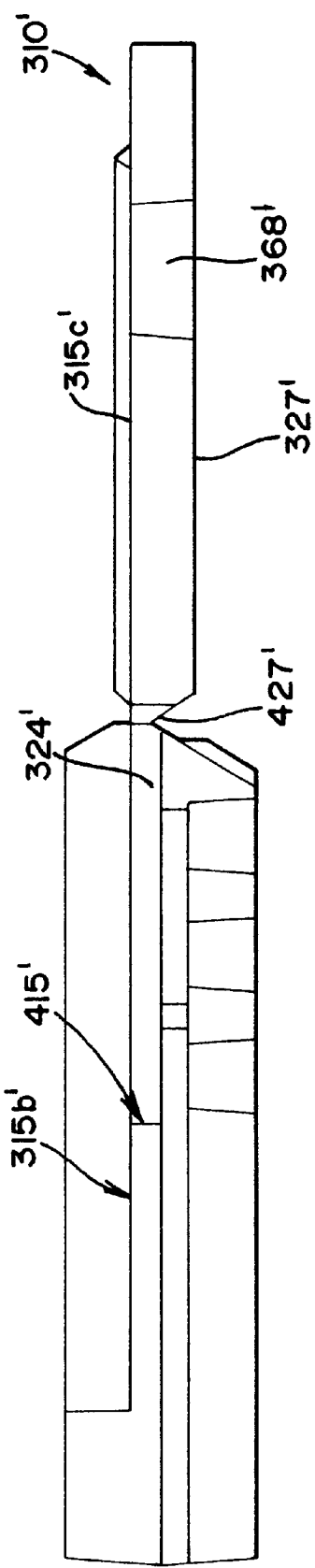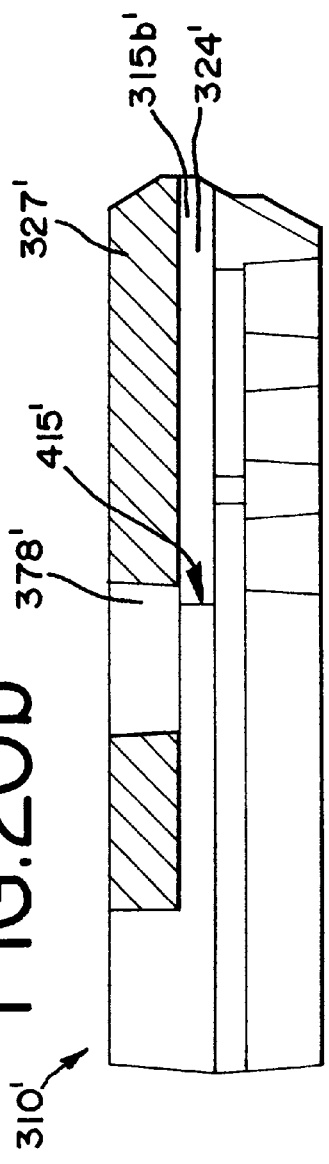

ELECTROCHEMICAL SENSOR AND METHOD THEREOF

CROSS-REFERENCE TO RELATED APPLICATION

This is a continuation-in-part of U.S. Ser. No. 09/820,372, filed Mar. 23, 2001, and entitled "Electrochemical Sensor and Method Thereof."

TECHNICAL FIELD

The present invention generally relates to electrochemical sensors and, in particular, to molded electrochemical sensors for detection or measurement of analytes in test samples, such as fluids and dissolved solid materials, and the methods of making and using these sensors.

BACKGROUND OF THE INVENTION

Electrochemical sensors are used to determine the concentrations of various analytes in testing samples such as fluids and dissolved solid materials. For instance, electrochemical sensors have been made for measuring glucose in human blood. Such sensors have been used by diabetics and health care professionals for monitoring blood glucose levels. The sensors are usually used in conjunction with a meter, which measures light reflectance, if the strip is designed for photometric detection of a die, or which measures some electrical property, such as electrical current, if the strip is designed for detection of an electroactive compound.

Typically, electrochemical sensors are manufactured using an electrically insulating base upon which conductive inks such as carbon and silver are printed by screen printing to form conductive electrode tracks or thin strips of metal are unrolled to form the conductive electrode tracks. The electrodes are the sensing elements of the sensor generally referred to as a transducer. The electrodes are covered with a reagent layer comprising a hydrophilic polymer in combination with an oxidoreductase or a dehydrogenase enzyme specific for the analyte. Further, mounted over a portion of the base and the electrodes is an insulating layer.

Precision and accuracy of electrochemical measurements to a great extent rely on the reproducibility of the electrode surface area on a microscopic scale. Variations in the morphology of the electrode can result in very significant changes in the electrochemical signal readout. Screen-printing has made significant in-roads in the production of sensors for determining glucose. The wide use of screen-printing stems from the ability to mass-produce relatively inexpensive sensors. The use of metal strips unrolled from large rolls has also been employed to mass produce such sensors.

While many advances have been made in the field of screen printing and conductive ink production, the technology still suffers from poor reproducibility of the electrode surface area, dimensional variations, thickness variations, micro-cracks, and shrinkage due to the repetitive and high temperature curing processes involved in using film printing technology. Loss of solvent during printing is another factor that leads to variations in the thickness of electrodes.

Sensor development using printing technology requires several passes of different conductive inks demanding different screens. Slight variations in positioning the screens can lead to substantial errors in IR drop and the applied potentials. Wear and tear of these screens is another source of error. Also, sensor strip production by screen printing suffers from a high level of raw material waste. Generally, for every gram of ink used, there is a gram of ink wasted. Manufacture of such sensors also involves several lamination processes that add to the production complexity and cost of the final product.

SUMMARY OF THE INVENTION

The present invention is an electrochemical sensor that provides for the determination of various analyte concentrations in a testing sample such as fluids and dissolved solid materials. The sensor is designed to facilitate production in large quantities using reliable and cost effective injection molding manufacturing methods. The present invention includes an injection molded plastic strip or body, at least two electrodes, an enzyme, and if desired, an electron transfer mediator. The body includes a cavity or reaction zone for receiving a fluid sample. The electrodes are at least partially embedded within the plastic body and extend into the reaction zone where they are exposed to a test sample. Also contained within the reaction zone is an enzyme capable of catalyzing a reaction involving a compound within the fluid sample.

Specifically, the device cooperates with an electronic meter capable of measuring the difference between the electrical properties of the electrically conductive electrodes within the device. The device, a sensor, includes at least two, and preferably three, spaced apart electrically conductive electrodes, a body having two ends of insulative material molded about and housing the electrodes, means for connecting the meter to the housing, means for receiving a fluid sample, and means for treating one or more electrodes with one or more chemicals to change the electrical properties of the treated electrodes upon contact with the fluid sample. One end of the housing has the means for connecting the meter and the opposite end of the housing has the means for receiving the fluid sample. The means for connecting the meter is a plug formed in the housing exposing the electrodes outside the body.

The sensor is molded and can be a single, unitary piece or two pieces. In the two piece construction, an end cap is attached to the body. In the single piece construction, the body pivots about a hinge and connects onto itself. Protuberances formed in a portion of the body cooperate with troughs to ensure proper alignment.

A capillary inlet is constructed at one end of the sensor to draw the fluid sample into the body upon contact with the fluid sample. The capillary inlet is molded into the end of the body and is in communications with a reaction zone. This reaction zone is a channel formed in the body about the electrodes and is adapted for reacting with the fluid drawn into the body by the capillary force. While the reaction zone may be formed above or below the electrodes, the preference has been to construct it above the electrodes. The capillary has a vent for relieving pressure.

As noted, the electrodes are molded into the plastic. In one embodiment, the electrodes are conductive wires. In another embodiment, the electrodes are constructed from a metal plate. The electrodes may be coated with a different conductive material to enhance their performance.

Apertures are formed in the body of the sensor to permit the holding of the electrodes during the molding process. Apertures may also be formed in the body to chemically treat one or more electrodes in the reaction zone before or after the molding process. Adding chemicals (e.g., reagents with and without enzymes) changes the electrical properties of the treated electrodes upon contact with the fluid sample. In the preferred embodiment, the enzyme is applied to the outer surface of one of the electrodes. An antibody may also be applied to another of the electrodes. An electron mediator may further be applied to the outer surface of one or more of the electrodes.

In another embodiment in accordance with the invention, the sensor provides fill detection. Fluid drawn into the capillary inlet and the reaction zone contacts the edges of the electrodes, and upon reaching the lower end of the reaction zone, the area farthest from the capillary inlet, activates the meter. When the fluid comes in contact with the last electrode in the capillary space, it closes an open circuit in the electrochemical cell causing current to flow through the cell. The flow of current in the cell triggers the meter, signaling that the capillary chamber is filled with fluid. The vent could also be used for a visual detection of fluid fill.

The methods of making and using the electrochemical sensor are also disclosed. The method of making the device includes the steps of positioning at least two spaced apart electrically conductive electrodes in a mold, before or after molding treating at least one of the electrodes with one or more chemicals to change the electrical properties of the treated electrode upon contact with a fluid sample, and molding a body of insulative material with two ends around the electrodes with one end having therein means for receiving a fluid sample. As before, the body is molded in two pieces, with a body and end cap for attaching to one another after the molding is completed, or in a single, unitary piece.

BRIEF DESCRIPTION OF THE DRAWINGS

In the accompanying drawings forming part of the specification, and in which like numerals are employed to designate like parts throughout the same, FIG. 1 is an enlarged top plan view of a first embodiment of an electrochemical sensor made in accordance with the teachings of the present invention;

FIG. 2 is a sectional end view of the electrochemical sensor of FIG. 1 taken along plane 2—2;

FIG. 3 is a sectional end view of the electrochemical sensor of FIG. 1 taken along plane 3—3;

FIG. 4 is a sectional end view of the electrochemical sensor of FIG. 1 taken along plane 4—4;

FIG. 5 is a sectional end view of the electrochemical sensor of FIG. 1 taken along plane 5—5;

FIG. 6 is a sectional side view of the electrochemical sensor of FIG. 1 taken along plane 6—6;

FIG. 7 is an enlarged top plan view of a second embodiment of an electrochemical sensor made in accordance with the teachings of the present invention;

FIG. 8 is an end elevation view of the electrochemical sensor of FIG. 7;

FIG. 9 is a side elevation view of the electrochemical sensor of FIG. 7;

FIG. 10 is a bottom plan view of the electrochemical sensor of FIG. 7;

FIG. 11 is a sectional end view of the electrochemical sensor of FIG. 7 taken along plane 11—11;

FIG. 12 is a sectional end view of the electrochemical sensor of FIG. 7 taken along plane 12—12;

FIG. 13 shows an enlarged top plan view of a third embodiment of an electrochemical sensor made in accordance with the teachings of the present invention;

FIG. 14 shows an enlarged bottom plan view of the electrochemical sensor of FIG. 13;

FIG. 15 is a sectional side view of the electrochemical sensor of FIG. 13 taken along plane 15—15;

FIG. 16 is a sectional end view of the electrochemical sensor of FIG. 13 taken along plane 16—16;

FIG. 17 shows a top plan view of a third embodiment of an electrochemical sensor made in accordance with the teachings of the present invention;

FIG. 18 shows an enlarged bottom view of the electrochemical sensor of FIG. 17;

FIG. 19 shows a sectional side view of the electrochemical sensor of FIG. 17 taken along plan 19—19; and, FIGS. 20a, b show a magnified view of the terminal end portion of the sensor of FIG. 17 having the end cap (a) extended away from the body and (b) secured to the body.

DETAILED DESCRIPTION

While this invention is susceptible of embodiments in many different forms, there is shown in the drawings and will herein be described in detail preferred embodiments of the invention with the understanding the present disclosure is to be considered as an exemplification of the principles of the invention and is not intended to limit the broad aspect of the invention to the embodiments illustrated.

The First Embodiment

Referring to FIGS. 1–6, an electrochemical sensor in accordance with the present invention, first embodiment, is depicted. FIG. 1 shows the sensor 10 as though it were made out of clear plastic, permitting one to look inside it. As discussed herein, the internal components and hidden external components would not normally be visible looking down on the sensor 10. This rendition would be similar to a view taken along plane x—x in FIG. 2.

The sensor or test strip of the first embodiment 10 includes an injection molded plastic body 12, opaque or preferably translucent, having a meter attachment end or plug end 14 and a fluid sample receiving end 16. The body has a bottom surface 13, a top surface 15 and a tapered portion 20 connecting a first top surface 15a to a second top surface 15b, the first top surface being lower than the second top surface, and a third top surface 15c, also lower than the second top surface. The body 12 contains three spaced apart electrodes 30,31,32. The plug end 14 of the body 12 includes a pair of tapered side edges 18,19 and a wedge shaped top portion 20. The tapered side edges 18, 19 facilitate a user inserting the sensor's plug end 14 into the socket cavity of a conventional meter (not shown). Moreover, the wedged portion 20 of the sensor serves as a stop, and frictionally holds the sensor 10 within the socket cavity of the meter.

The fluid sample receiving end 16 of the sensor 10 includes an electrochemical reaction zone 24 adjacent the terminal end 16 of the body. This reaction zone 24 is a channel formed in the third top surface 15c and about/adjacent the electrodes 30,31,32 in the body 12 for analyzing the fluid drawn into the body 12 for a particular analyte. While the reaction zone may be formed above or below the electrodes, the preference has been to construct it above the electrodes. An end cap 27 is welded [by ultrasonics or adhesive] over the reaction zone 24 and onto the third top surface 15c. The top of the end cap 27 aligns with the top 15,15b of the body 12. The end cap 27 is preferably made of the same material as the molded body 12 and attached thereto by ultrasonic welding or gluing.

While the cap 27 is shown as a separate piece, it can also be constructed as part of the body 12 and hingeably connected to the body such that it can be pivoted onto the third top surface 15c and attached [e.g., see The Second Embodiment]. In this manner, the entire sensor can be made at one time and as one molded, unitary piece.

A capillary opening 28 is formed in the terminal end 16 of the sensor 10 when the cap 27 is welded (or folded) to the body 12. This capillary opening leads to the reaction zone 24. Preferably, the sensor 10 is a capillary fill device, that is, the reaction zone 24 is small enough to draw a fluid sample into the zone when the capillary opening or inlet 28 is placed in contact with the fluid being tested, such as a drop of blood. Accordingly, if one wants to test his/her blood, s/he touches the terminal end 16 to the blood and the blood is drawn into the sensor 10 and reaction zone 24 through the capillary opening 28. This is much easier than placing the sample (such as blood) on the sensor and on a target zone as in the prior art. To effectuate the capillary effect with the capillary opening 28 to the reaction zone 24, a vent 29 is constructed into the cap 27. This vent is in communication with the reaction zone 24. This vent 29 releases air pressure as the reaction zone 24 draws and fills with fluid. For additional discussion regarding capillary filling, see U.S. Pat. Nos. 4,254,083; 4,413,407; 4,473,457; 5,798,031; 5,120,420; and 5,575,895, the disclosures of which are hereby incorporated by reference.

Mostly encased within the injection molded body 12 are a plurality of electrically conductive leads or electrodes 30,31,32. Preferably, the body 12 is molded about these leads 30,31,32. As noted, these leads are spaced from one another. They 30,31,32 are primarily encased in the body 12 and run from the plug end 14 to the reaction zone 24, just before the terminal end 16. The leads' 30,31,32 ends 26 are positioned just before the terminal end 16 of the sensor.

The conductive leads 30,31,32 consist of an electrically conductive material like metal or metal alloy such as platinum, palladium, gold, silver, nickel, nickel-chrome, stainless steel, copper or the like. Moreover, each lead preferably consists of a single wire, or in an alternative preferred embodiment (See The Second Embodiment), a stamped metal member plated with gold or the like. In the first embodiment, the outer leads 30 and 32 are equally spaced from the inner lead 31 with the spacing of the leads at the fluid sample receiving end 16 of the body 12 being closer together than at the meter attachment end 14.

Segments 33 of the leads 30,31,32 are exposed about the plug end 14 of the body 12 to provide contact surface areas 34,35,36 respectively with the meter (not shown). Preferably, the exposed contact surface areas 34,35,36 extend from the tapered top portion 20 of the body 12 to the plug end 14 of the body 12 on or partially embedded into the first top surface 15a. Specifically, the body 12 may be molded such that the segments 33 of the leads 31,31,32 are embedded (partially molded into the first top surface 15a) and held by the body 12 opposite the contact surface areas 34,35,36. In this manner, the leads are exposed for contact with the meter and maintained in a position without the use of adhesives or welding.

The portion of the leads 30,31,32 between the sensor plug end 14 and the fluid sample receiving end 16 are embedded within the plastic injection molded body 12. Accordingly, the body 12 is constructed of an electrically insulating injection moldable plastic.

Certain structural support components are molded within the body 12 of the sensor 10 to hold and maintain the leads 30,31,32 within the body, in spaced relationship to one another, during and after the molding process. Specifically, guide blocks 42 and alignment pins 44 are molded within the body 12 for proper mounting of the leads 30,31,32. Apertures are also formed in the top surface 15 and bottom surface 13 of the body 12 for permitting the ingress and egress of fingers into the mold during the molding process (to be discussed below). In particular, a first aperture 46 is molded into the second top surface 15b and a second aperture 48 and third aperture 50 are formed into the bottom surface 13 of the body 12. Once the molding is completed, each of these apertures 46,48,50 is covered up or sealed with plastic (e.g., the same plastic used in the molding process) or left open. Their 46,48,50 sizes are relatively small; leaving them open should not cause any safety issues or affect the sensor's ability. Fingers cannot fit into the apertures and debris from the outside will likely be unable to enter the apertures and contact the leads 30,31,32.

Within the reaction zone 24, one lead 30 serves as a primary working electrode 52, a second lead 31 acts as a reference or counter electrode 53, and the third lead 32 serves as an auxiliary, secondary or second working electrode 54. Desirably, the conductive leads 30,31,32 (or electrodes 52,53,54) are the only leads (electrodes) coming into contact with the test sample of fluid entering the sensor 10. The electrodes 52,53,54 are electrically insulated from the rest of the sensor 10 by molded plastic to ensure a signal carried by the leads arises only from that portion exposed to the test sample in the electrochemical reaction zone 24.

In the embodiment, an enzyme 56 is applied to the outer surface of the primary working electrode 52 and, if desired, an electron transfer mediator. The enzyme can consist of, for instance, flavo-proteins, pqq-enzymes, haem-containing enzymes, oxidoreductase, or the like. For additional discussion regarding mediators, see U.S. Pat. Nos. 4,545,382 and 4,224,125, the disclosures of which are hereby incorporated by reference. In an alternative embodiment, an antibody 57 can be applied to the outer surface of the secondary working electrode 54. As such, the reaction zone 24 can contain antibodies, enzyme-antibody conjugates, enzyme-analyte conjugates, and the like. It should be noted that an enzyme 56 can also be applied to the second working electrode 54 and an antibody can be applied to the outer surface of the primary working electrode 52.

As will be appreciated by those having skill in the art, the enzyme 56 is specific for the test to be performed by the sensor 10. For instance, the working electrode 52, or secondary working electrode 54, or both, can be coated with an enzyme 56 such as glucose oxidase or glucose dehydrogenase formulated to react at different levels or intensities for the measurement of glucose in a human blood sample. Thus, as an individual's body glucose concentration increases, the enzyme 56 will make more products. The glucose sensor is used with a meter to measure the electrochemical signal, such as electrical current, arising from oxidation or reduction of the enzymatic turnover product(s). The magnitude of the signal is directly proportional to the glucose concentration or any other compound for which a specific enzyme has been coated on the electrodes.

In an embodiment, the enzyme 56 can be applied to the entire exposed surface area of the primary electrode 52 (or secondary electrode 54). Alternatively, the entire exposed area of the electrode may not need to be covered with the enzyme as long as a well defined area of the electrode is covered with the enzyme.

In a further embodiment and as shown in the prior art, an enzyme 57 can be applied to all the electrodes 52,53,54 in the reaction zone 24 and measures can be taken by a meter.

In the preferred embodiment, one of the working electrodes (52 or 54) is selectively coated with the enzyme 57 carrying a reagent with the enzyme and the other working electrode (54 or 52) is coated with a reagent lacking the respective enzyme. As such, with a meter, one can simultaneously acquire an electrochemical signal from each working electrode and correct for any "background noise" arising from a sample matrix. Thus, the potential or current between the reference and the electrode without the enzyme can be compared with the potential or current between the reference and the electrode with the enzyme. The measuring and comparing of the potential and current differences are well known to those skilled in the art.

As indicated above, the sensor 10 is used in conjunction with a meter capable of measuring an electrical property of the fluid sample after the addition of the fluid sample into the reaction zone 24. The electrical property being measured may be, for example, electrical current, electrical potential, electrical charge, or impedance. An example of measuring changes in electrical potential to perform an analytical test is illustrated by U.S. Pat. No. 5,413,690, the disclosure of which is hereby incorporated by reference.

An example of measuring electrical current to perform an analytical test is illustrated by U.S. Pat. Nos. 5,288,636 and 5,508,171, the disclosures of which are hereby incorporated by reference.

The plug end 14 of the sensor 10 can be inserted and connected to a meter, which includes a power source (a battery). Improvements in such meters and a sensor system are found in U.S. Pat. Nos. 4,999,632; 5,243,516; 5,366,609; 5,352,351; 5,405,511; and 5,438,271, the disclosures of which are hereby incorporated by reference.

Many analyte-containing fluids can be analyzed by the electrochemical sensor of the present invention. For example, analytes in human and animal body fluids, such as whole blood, blood serum and plasma, urine and cerebrospinal fluid may all be measured. Also, analytes found in fermentation products, food and agricultural products, and in environmental substances, which potentially contain environmental contaminants, may be measured.

The Molding Process of the First Embodiment

In the past, while recognized for its strength and durability, plastic injection molding of sensors has been difficult and thus avoided. One reason is the reluctance to mold around the conductive wires or plates. The industry choice has been to make such sensors like sandwiches, having a top and bottom piece with the insides (conductive elements) being formed on one of the pieces or placed between the pieces. The sandwich-like sensor is then assembled together and sealed closed, such as with an adhesive.

The present invention molds the sensors with the conductive elements inside the mold during the molding process. The advantages are many. In addition to making a stronger more durable sensor, such a process reduces labor involvement and steps and produces a more consistent product.

While multiple sensors 10 can be produced with one mold, the making of a single sensor will be discussed. The mold has the shape of the body 12. The conductive wires 30,31,32 for the electrodes are first molded into the product. Specifically, the wire leads are fed into the mold and placed on or between figures [not shown] projecting into the mold through the openings in the mold (corresponding to the apertures 46,48,50) to hold the wires in place and level during the set-up and molding process. In particular, the bottom apertures permit the fingers projecting into the mold to support the wires and the top apertures permit the fingers projecting into the mold to hold the wires. The liquid plastic is injected into the mold where it fills the mold. The plastic is then cooled.

Once the plastic has formed and hardened, the fingers are pulled from and exit the mold through the openings (apertures 46,48,50). The molded sensor 12 is next ejected from the mold.

The reagents are next applied to the electrodes after the molding process is finished. First, after molding is finished, the cap is treated with a surfactant that facilitates pulling or drawing the fluid (e.g., test blood) into the capillary gap at the end of the sensor. Then, the reagents (including the enzyme) are applied to the electrodes.

The end cap 27 is thereafter connected to the main body 12 and any undesirable openings in the sensor can be sealed closed by the same plastic used for the mold. In the alternative, the chemicals can be applied to the wires after the end cap is married to the body. Any extraneous wire(s) projecting from the sensor can be cut and removed. Then, any desired writings on the sensor (e.g., manufacturing codes, product name, etc.) can then be applied to the sensor by conventional means.

The Second Embodiment

Referring to FIGS. 7–12, an electrochemical sensor in accordance with the present invention, second embodiment, is depicted. In these figures, components similar to those in the first embodiment (10) will be identified with the same reference numbers, but in the 100 series. Specifically, FIG. 7 shows the sensor 110 as though it were made out of clear plastic, permitting one to look inside it. As noted previously, the internal components and hidden external components would not normally be visible looking down on the sensor 110. The sensor of the second embodiment 110 includes a molded plastic body 112 having a meter attachment end or plug end 114 and a fluid sample receiving end 116. The body has a bottom surface 113 and a top surface 115. An end cap 127 is integral to the body 112 and molded with the body. A hinge 227 permits the pivoting of the end cap onto the main body as will be explained. Specifically, the top surface 115 of the sensor 110 has three top surfaces 115a,115b,115c. The first top surface 115a runs most of the length of the body and terminates at a ledge 215; the second top surface 115b is positioned below or is lower than the first 115a; and, the third top surface 115c is separated from the other two top surfaces 115a,115b by the hinge 227. During construction of the sensor 110, the end cap 127 is rotated about the hinge such that the third top surface 115c abuts the second top surface 115b, face-to-face, and rests adjacent the ledge 215 of the top surface 115a. The bottom surface 13a of the cap 127 thus becomes the top surface adjacent the first top surface 115a. See FIG. 8. A pair of tapered protuberances 125 formed in the end cap 127 and a pair of tapered troughs 122 formed in the main body 112 align and mate when the cap is folded into place. This facilitates and ensures correct alignment of the hinged parts.

The body 112 contains three spaced apart electrodes 130,131,132. The plug end 114 of the body 112 includes a pair of tapered side edges 118,119 to facilitate a user inserting the sensor's plug end 114 into the socket cavity of a conventional meter (not shown).

The fluid sample receiving end 116 of the sensor 110 includes an electrochemical reaction zone 124 adjacent the terminal end 116 of the body. This reaction zone 124 is a channel formed in the second top surface 115b and about/ adjacent the electrodes 130,131,132 in the body 112 for reacting with the fluid drawn into the body 112. While this reaction zone may be formed above or below the electrodes, the preference has been to construct it above the electrodes. A ridge 327 is formed on the top surface (third top surface 115*c*) of the end cap. This ridge prevents any fluid from leaving the reaction zone 124 or debris from entering the reaction zone once the end cap 127 is welded [by ultrasonics or adhesive] onto the second top surface 115*b*. When the end cap is folded, it is welded into position along the side surfaces of the piece 110. Thus, the ridge can be collapsed during welding and not affect the performance of the sensor. An optional channel 327*a* may be constructed in the third top surface 115*c* to increase the height of the reaction zone 124.

A capillary opening 128 is formed in the terminal end 116 of the sensor 110 when the cap 127 is folded and welded into place. This capillary opening leads to the reaction zone 124. The width of the opening 128 is approximately the same as the length of the sensing electrodes 130,131,132 exposed to the test fluid in the reaction zone 124. The sensor 110 of the second embodiment is also a capillary fill device, that is, the reaction zone 124 is small enough to draw a fluid sample into the zone when the capillary opening 128 is placed in contact with the fluid being tested. A vent 129 provided in the cap 127 is in communication with the reaction zone 124 to release pressure as the reaction zone 124 draws and fills with fluid. Preferably, the bottom or base of the capillary inlet is flush with the top surface of electrodes 130,131,132.

Mostly encased within the injection molded body 112 is an electrically conductive plate (stamped or cast) having leads or electrodes 130,131,132. The body 112 is molded around the plate and these leads 130,131,32. The conductive plate is a single piece of material; it includes the leads 130,131,132 and connecting segments 230 and 231. When the sensor is made, the segments are connecting the leads. After molding, the segments 230,231 are cut and/or removed so that the leads are distinct and separated from one another. If they were connected, the system would short circuit.

The electrodes 130,131,132 are primarily encased in the body 112 and run from the plug end 114 into the reaction zone 124, just before the terminal end 116. The leads 130,131,132 may be widened if desired in the reaction zone to expose more surface area to the fluid and chemicals contacting one another in the zone. The leads 130,131,132 can be as wide as the sensing parts. These leads 130,131,132 are an electrically conductive material like metal or metal alloy such as platinum, palladium, gold, silver, nickel, nickel-chrome, stainless steel, copper or the like. To enhance their performance and sensitivity, they may also be coated, e.g., made of copper and coated with gold. In the second embodiment, the leads 130,131,132 are spaced from and parallel to one another.

Segments 133 of the leads 130,131,132 extend outwardly from the body 112 from the plug end 114 of the sensor 110 and are exposed to provide contact surface areas 134,135, 136 respectively with the meter (not shown). These leads can also be embedded in the molded plastic such that their upper surfaces are exposed in portions.

As before, the portion of the leads 130,131,132 between the sensor plug end 114 and the fluid sample receiving end 116 are embedded, or encased, within the plastic injection molded body 112; the body 112 is constructed of an electrically insulating injection moldable plastic.

Apertures are formed in the top surface 115 and bottom surface 113 of the body 112 for permitting the ingress and egress of fingers into the mold during the molding process. In particular, a set (3) of first apertures 146 and a set (3) of second apertures 147 are molded into the top surface 15*a;* a third aperture 148 and fourth aperture 150 and a set (3) of fifth apertures 160,161,162 are formed into the bottom surface 113 of the body 112. Once the molding is completed, each of these apertures 146,147,148,150 can be covered up with plastic (e.g., the same plastic used in the molding process) or left open.

Within the reaction zone 124, one outer lead 130 serves as a primary working electrode 152, the center lead 131 acts as a reference or counter electrode 153, and the other outer lead 132 serves as an auxiliary or secondary or second working electrode 154. These conductive leads 130,131,132 (or electrodes 152,153,154) are the only leads (electrodes) coming into contact with the test sample of fluid entering the sensor 110. The electrodes 152,153,154 are electrically insulated from the rest of the sensor 110 by molded plastic to ensure a signal carried by the leads arises only from that portion exposed to the test sample in the electrochemical reaction zone 124.

As with the first embodiment, an enzyme 156 is applied to the outer surface of the primary working electrode 152 and, if desired, an electron transfer mediator. An antibody 157 may also be applied to the outer surface of the secondary working electrode 154. An enzyme 156 can also be applied the second working electrode 154 and an antibody to the outer surface of the primary working electrode 52.

The enzyme 156 can be applied to the entire exposed surface area of the primary electrode 152 (or secondary electrode 154). Alternatively, the entire exposed area of the electrode may not need to be covered with the enzyme as long as a well defined area of the electrode is covered with the enzyme. Or, an enzyme can be applied to all the electrodes 152,153,154 in the reaction zone 124 and measurements can be taken by a meter. Preferably, one of the working electrodes (152 or 154) is selectively coated with the enzyme carrying a reagent with the enzyme and the other working electrode (154 or 152) is coated with a reagent lacking the respective enzyme.

The sensor 110 is used in conjunction with a meter capable of measuring an electrical property of the fluid sample after the addition of the fluid sample into the reaction zone 124. The plug end 114 of the sensor 110 is inserted and connected to a meter, as before with the first embodiment.

The Molding Process of the Second Embodiment

The mold has the shape of the body 112. The conductive 130,131,132 leads/electrodes (in the form of a plate with the joining extensions 230,231 for the electrodes) are first treated with any coatings (metal). The chemicals/reagents (with and without enzymes) may also be applied before molding; or, they can be applied after the molding. The plate is fed into the mold and placed on or between fingers (not shown) projecting into the mold through the openings in the mold (corresponding to the apertures 146,147,148,150) to hold the plate in place and level during the set-up and molding process. Knives or punches (not shown) are also inserted through the top surface of the mold (outline of opening formed by the knives/punches 170). These knives punch and sever the jointing extensions 230,231 and hold the bent portions in place during molding (see FIG. 11). As before, the bottom apertures permit the fingers projecting into the mold to support the plate with leads and the top apertures permit the fingers projecting into the mold to hold the plate and leads. The liquid plastic is injected into the mold where it fills the mold. The plastic is then cooled.

Once the plastic has formed and hardened, the fingers are drawn from the mold through the openings (apertures 146, 147,148,150,160,161,162). The knives/punches are drawn through the upper surface openings 170. Once the knives/punches are removed, the cut or skived extensions 230,231 disposed between the leads 130,131 and 131,132 ensures the leads are kept separate. The molded sensor 112 is then ejected from the mold and any undesirable openings in the sensor can be sealed closed by the same plastic used for the mold. In the preferred alternative, the critical reagents are applied to the sensors in the reaction zone 124 above the leads. A surfactant can be used to treat the capillary inlet to facilitate the capillary function. Any extraneous metal projecting from the sensor can be cut and removed. Then, any desired writings on the sensor (e.g., manufacturing codes, product name, etc.) can then be applied to the sensors by conventional means.

The Third Embodiment

Shown in FIGS. 13–20 is a third embodiment of an electrochemical sensor in accordance with the present invention. These figures use the same reference numbers, but in the 300 series, to identify components that are similar to those in the previous embodiments. FIGS. 13 and 17, respectively, depict the sensor 310,310' in its entirety, including its internal components not normally visible when looking down on the sensor 310,310'.

In the third embodiment sensor 310,310' is used in conjunction with a meter capable of measuring an electrochemical property of the fluid sample after the fluid sample is drawn into the reaction zone 324,324'. The sensor 310,310' includes a molded plastic body 312,312' having a meter attachment end or plug end 314,314' and a fluid sample receiving end 316,316'. The plug end 314,314' is insertable or connectable to a meter, as with the two prior embodiments. The body also has a bottom surface 313,313' and a top surface 315,315'. The body 312,312' is molded as a unitary, single piece having two portions—(a) an electrode-encasing housing 317,317' and (b) an end cap 327,327' pivotably attached to the electrode housing 317,317' at the fluid sample receiving end 316,316' at hinge 427,427'. In an alternative embodiment, the electrode housing and the end cap may be separate pieces that are securely attachable to one another. The side edges 318,319,318',319' near the plug end 314,314' of the body 312,312' are tapered so the plug end 314,314' inserts more easily into the socket cavity of a conventional meter (not shown). The end cap 327,327' may have a "notch" 326,326' formed into the outermost edge opposite the body to facilitate molding.

FIG. 15 shows a longitudinal sectional side view of sensor 310. The top surface 315 has three sections or surfaces including 315a,315b,315c. The first top surface 315a accounts for a predominate portion of the body, as it extends from the plug end 314 to a ledge 415. The second top surface 315b runs from the ledge 415 to the hinge 427, on a plane lower than 315a. The third top surface 315c extends across one surface of the end cap 327, from the hinge 427 to the outermost edge of the end cap.

The hinge 427 allows the end cap to be folded onto the body so that the third top surface 315c abuts the second top surface 315b, face-to-face, and the edge of the end cap rests substantially adjacent the ledge 415, as in the second embodiment discussed above. In the finished sensor, the bottom surface 313a of the end cap 327 becomes part of the top surface of the body and rests adjacent the first top surface 315a, in essentially the same plane, as shown in FIG. 15.

When the end cap is folded onto the second top surface 315b of the body, adjacent the terminal end 316 of the body, a channel termed the "electrochemical reaction zone" 324 forms in the body. The reaction zone 324 is bound on one side by the second top surface 315b and, on the opposite side, by top surface of the end cap 327. The reaction zone has a volume defined by the shape of the body. Alternatively, if desired, the cap may be shaped so that when it is pivoted onto the body, the cap defines the volume of the reaction zone; or the shape of both the cap and the body may form the volume of the reaction zone.

Running throughout the longitudinal axis of the body 312 are the leads 330,331,332, which are spaced apart in fixed relation to each other. The leads 330,331,332 terminate in the reaction zone 324. FIGS. 17–19 show a sensor in accordance with the invention having two electrodes 330', 331'.

In the reaction zone or cavity 324, the leads are not entirely embedded in the insulative material of the body. In the reaction zone 324, at least a portion of the leads—e.g., the tips, sides, or other portion—is exposed therein as sensing electrodes 330,331,332 for contacting fluid sample drawn into the body 312. The reaction zone 324 lies primarily in the bottom lengthwise portion of the detector. Although the reaction zone may be formed above or below the electrodes, it is preferably constructed below the electrodes.

The cap 327 is folded onto the body and securely affixed to the body to form a substantially tight seal. As result of this configuration, a capillary opening 328 forms in the terminal end 316 of the sensor 310. The capillary opening 328 leads to the reaction zone 324 where the edges of the sensing electrodes 330,331,332 are exposed to the test fluid. The width of the capillary opening 328 is approximately the same as that of the sensing electrodes 330,331,332.

Body 312 may also have proturberances to ensure correct alignment of the surfaces when folded about the hinge. The protuberances are typically disposed on at least one of (a) the surface of the end cap that folds onto the body and (b) the top third surface of the body onto which the end cap folds that is covered by the end cap when folded onto the body. Although a variety of configurations are possible, in one embodiment, e.g., the protuberances may appear on both the end cap and the upper surface 315b of the body.

In one embodiment, shown in FIG. 13, the protuberance comprises a ridge 527 and a recessed surface 528 that mate when the cap is folded onto the body, to form the reaction zone. In this embodiment, the ridge 527 may be formed on the second top surface 315b along the periphery of the reaction zone 324, and the recessed surface may be formed on the cap 327, or vice versa. The ridge 527 may also sit in and be substantially aligned with a secondary ridge (not shown), which increases the height of ridge 527.

In the finished sensor 310, the ridge 527 mates with recessed surface 528 to form a seal, enclosing the reaction zone 324 within the body. Alternatively, the ridge 527 and recessed surface 528 may be further welded together by, e.g., ultrasonic energy, adhesive, or any other suitable techniques. The seal, so formed, prevents the reaction zone 324 from losing fluid or accepting debris. During welding, the ridge 527 fuses into the recessed surface 528 without affecting the performance of the sensor.

In yet another aspect of the third embodiment, shown in FIGS. 17–20, the proturberance is an energy director 529' formed on at least one of the end cap and the upper surface 315b' of the body. A variety of configurations is possible such as one wherein the energy director is disposed entirely on the body for fusing with the cap when pivoting of the cap onto the body. As shown in the embodiment depicted in FIGS. 17–19, the energy director 529' typically comprises at least one protruding ridge extending preferably along the periphery of the end cap. Typically, the energy director extends along the three unattached sides of the end cap, although it may extend across portions of the sides. In the embodiment depicted, the energy director 529' begins at hinge 427' and extends on the end cap 327' directionally away from the hinge 427' and across the end farthest from the hinge.

When the cap is pivoted onto the body, the energy director 529' is generally melted by, e.g., ultrasonic energy or other conventional means, to induce formation of a strong, leak-free joint bond between the bottom surface and cap surface. The bond so formed seals the fluid within the chamber, preventing fluid from diffusing out from the reaction zone. Alternatively, a seal may be formed by the application of adhesives.

The sensor of the third embodiment is also a capillary fill device; i.e., when the capillary opening 328' is placed in contact with the fluid being tested, the reaction zone 324' draws the fluid sample into the zone. Included in cap 327' is sample fill vent 368'. When cap 327' is folded onto body 312', at least a portion of the sample fill vent 368' is in communication with the reaction zone to form a depressurization vent 378' for releasing air from the reaction zone as the zone fills with fluid. The depressurization vent 378' extends between one edge of the sample fill vent 368' and the ledge 415' of the reaction zone, which is the back wall of the reaction zone farthest from the terminal end 316'. FIGS. 20a, b show a magnified view of the terminal end portion of the sensor 310' of FIG. 17. FIG. 20a shows the cap 327' extended away from the body, and FIG. 20b shows the cap 327' folded onto the body of the sensor.

The depressurization vent 378' provides for fill detection in the third embodiment. Fluid drawn through the capillary opening 328' travels along the capillary, preferably in the lower portion of the body 312', to the reaction zone 324' where it contacts the electrodes 331',332' of sensor 310' (or electrodes 330,331,332 of sensor 330,331,332). Preferably, the surface of the electrodes facing the upper surface 315' of the body is flush with the bottom periphery of the capillary inlet 328'. As sample fluid enters the reaction zone 324', it travels toward the end of the reaction zone farthest from the capillary inlet until it reaches the depressurization vent 378'. As the fluid displaces air present in the depressurization vent 378', the fluid contacts at least one of the electrodes in the reaction zone, so as to close an open circuit in the sensor 310' and cause current to flow through the sensor. The flow of current in the sensor activates the meter, signaling that the capillary chamber or reaction zone is sufficiently filled with fluid. The depressurization vent 378' may also be used to visually detect fluid fill in the reaction zone.

The injection molded body 312 is constructed of an electrically insulating injection moldable plastic. The body 312 is molded around the electrically conductive plate (stamped or cast) with its leads 330,331,332 so that the conductive plate is encased primarily within the body 312. The conductive plate is a single piece of material; it includes the leads 330,331,332 (330',331' in FIG. 18) and the connecting segments 430 and 431 (reference no. 432 in sensor 310'). After the sensor is made, the segments 430 and 431 interconnecting the leads are cut and/or removed to separate the leads from one another. If the interconnecting segments remained intact during operation of the sensor, the system would short circuit.

The body may have a plurality of guides molded therein with at least one of the guides abutting against at least one of the leads.

The leads 330,331,332 extend longitudinally through the body 312 from the plug end 314 to the reaction zone 324, terminating just before the terminal end 316. The leads 330,331,332 are encased, or embedded, in the body 312 at a pre-determined distance from each other; they are generally parallel to one another though this is not necessary for operation of the sensor. In the reaction zone, a sufficient portion of the leads are exposed for contacting the fluid sample; the exposed portion includes, e.g., at least the tips, ends, or sides of the electrodes.

The electrodes 330,331,332 are an electrically conductive material such as metal or metal alloy; e.g., platinum, palladium, gold, silver, nickel, nickel-chrome, stainless steel, copper or the like. For enhanced performance and sensitivity, they may also be coated with a metal different from that composing the lead; e.g., a lead made of copper may be coated with gold. If desired, the width of the leads 330,331,332 may be widened or narrowed in the reaction zone 324 to expose more or less surface area to the fluid and chemicals therein. The leads 330,331,332 extending through the body can be as wide as the exposed portion within the reaction zone, which comprises the electrodes 330,331,332.

Each of the leads 330,331,332 terminates in a segment 333a,b,c that may extend outside the body 312 from the plug end 314 where the leads provide surface areas 334,335,336, respectively, for contact with the meter (not shown). Alternatively, the leads can be embedded in the molded plastic such that only a portion of each lead is exposed outside the body at the plug end 314; or the top surface of the leads comes in contact with the meter electrical contact leads.

Apertures molded into the top surface 315 and the bottom surface 113 of the body 312 permit fingers to be inserted into and removed from the mold during the molding process. The top surface 315a has two sets of apertures—first apertures 346 and second apertures 347—each having three individual openings or apertures. The bottom surface 313 has third aperture 348, fourth aperture 350, and fifth apertures, the latter including three individual apertures 360,361,362. Once the molding is completed, each of these apertures 346,347,348,350 is preferably left open. In a preferred embodiment, the apertures are closed to prevent accidental contact of the fluid with areas other than the electrodes in the reaction zone. The apertures may, alternatively, be covered such as with the same or a different material used in the molding process.

Within the reaction zone 324, conductive electrodes 330, 331,332 include a primary working electrode 352, a reference or counter electrode 353, and a secondary working electrode 354. In the reaction zone, the conductive electrodes 330,331,332 contact the test sample, in fluid form, as it enters the sensor 310. The signal carried by the electrodes arises in the reaction zone 324 from contact made by the exposed portion of the electrode with the test sample. In the reaction zone, one electrode, preferably the center electrode is a reference electrode. The reaction zone may also have one or, alternatively, two working electrodes; e.g., primary working electrode 352 and secondary electrode 354.

An enzyme, conjugated to another moiety, such as an antibody or antigen or an analyte, is applied to the outer surface of the primary working electrode 352, and if desired, an electron transfer mediator may be applied to the same electrode 352. An antibody may also be applied to the outer surface of the secondary working electrode 354 or otherwise present in the reaction zone. As such, the reaction zone 324 can contain antibodies, enzyme-antibody conjugates, enzyme-analyte conjugates, and the like.

The enzyme can be applied to the entire exposed surface of the primary electrode 352 or the secondary electrode 354. Alternatively, the enzyme is applied to a particular, defined portion of a working electrode. Or, an enzyme can be applied to all the electrodes 352,353,354 in the reaction zone 324. Preferably, one of the working electrodes (352 or 354) is selectively coated with the enzyme carrying a reagent with the enzyme, and the other working electrode (354 or 352) is coated with a reagent lacking the respective enzyme.

In yet another aspect of this third embodiment, the reaction zone or cavity 324 may itself be coated with a substance—such as a reagent, an antibody, or an enzyme—that reacts with certain constituents in the fluid sample to change the electrochemical properties of the sample. The resulting change is readily detected by the electrodes and measured by the meter.

The Molding Process of the Third Embodiment

The mold has the shape of the body 312. The conductive 330,331,332 leads (in the form of a composite plate with the joining extensions 430,431 for interconnecting the electrodes) are first treated or coated with a substance, which may be an enzyme, an antibody, or a chemical reagent, as examples. The chemicals/reagents (with and without enzymes) are generally applied after the molding.

The plate is fed into the mold and placed on or between fingers (not shown) that project into the mold through the openings in the mold, which correspond to the apertures 346,347,348,350,360,361,362. The fingers hold the plate in place, keeping it level during the set-up and molding process.

Knives or punches (not shown) are inserted through the top surface of the mold (outline of opening formed by the knives/punches 370). These knives punch and sever the joining extensions 430,431 and hold the bent portions in place during molding, as shown in FIG. 15. During the molding process, the bottom apertures allow the fingers to be projected into the mold to support the plate with leads; similarly, the top apertures allow the fingers to be projected into the mold to hold the plate in place with the leads. Liquid plastic is injected into the mold, filling it. The plastic is then cooled.

After the plastic has formed and hardened sufficiently, the fingers are removed from the mold through the openings; i.e., apertures 346,347,348,350,360,361,362. The knives/punches are drawn through and removed from the upper surface openings 370, leaving the cut or skived extensions 430,431 disposed between the leads 330,331 and 331,332. These cut extension keep the leads separated. The molded sensor 312 is then ejected from the mold, and any undesirable openings in the sensor can be sealed closed with the same plastic used for the mold.

In a preferred alternative, the critical reagents are applied to the sensor in the reaction zone 324 above the leads. A surfactant can also be applied to the capillary opening 328 to facilitate the capillary function. Any extraneous metal projecting from the sensor can be cut and removed. In addition, any desired writings or other designations on the sensor (e.g., manufacturing codes, product name, etc.) can be applied to the sensors by conventional means.

While the specific embodiments have been illustrated and described, numerous modifications come to mind without significantly departing from the spirit of the invention and the scope of protection is only limited by the scope of the accompanying claims. For instance, in another embodiment of the present invention, a sensor is designed for use with a light reflectance measuring meter for photometric detection of a dye contained within a fluid sample receiving well.

We claim:

1. An electrochemical device for cooperating with a meter to measure changes in electrochemical properties of a fluid sample as a result of chemical or enzymatic reactions, comprising:

a unitary single piece body of molded plastic insulative material with a first end and an opposing second end;

at least two electrically conductive electrodes substantially molded into with at least a part thereof encased by the plastic, wherein the electrodes are disposed in fixed longitudinal relation in the insulative material;

means for connecting a meter to the body;

means for receiving a fluid sample;

means for detecting when a sufficient amount of fluid sample has been received selected from the group consisting of (a) an electrical indication and (b) a visual indication; and, one or more substances deposited on at least one of the electrodes to react with the fluid sample to produce electrochemical changes correlative to the concentration of an analyte in the sample.

2. An electrochemical device for cooperating with a meter to measure changes in electrochemical properties of a fluid sample as a result of chemical or enzymatic reactions, comprising:

a body of insulative material with a first end and an opposing second end comprising an electrode housing and an end cap pivotably attached to the electrode housing at the first end of the body with both the electrode housing and the end cap being molded plastic;

at least two electrically conductive electrodes disposed in fixed longitudinal relation in the insulative material;

means for connecting a meter to the body;

means for receiving a fluid sample;

means for detecting when a sufficient amount of fluid sample has been received selected from the group consisting of (a) an electrical indication and (b) a visual indication; and one or more substances deposited on at least one of the electrodes to react with the fluid sample to produce electrochemical changes correlative t the concentration of an analyte in the sample.

3. The electrochemical device of claim 2 wherein the body has a hinge at the first end for permitting at least a portion of the body on one side of the hinge to pivot and connect onto a portion of the body on the other side of the hinge.

4. The electrochemical device of claim 3 further comprising at least one ridge and one recessed surface, each formed in the device on opposite sides of the hinge, such that when the body is pivoted about the hinge, said ridge and said recessed surface mate to form a reaction zone.

5. The electrochemical device of claim 2 further comprising at least one protuberance formed on at last one of the housing and the end cap, such that the end cap may be pivoted onto the housing and securedly attached thereto to form a reaction zone in the body.

6. An electrochemical device for cooperating with a meter to measure changes in electrochemical properties of a fluid sample as a result of chemical or enzymatic reactions, comprising:

a unitary single piece body of insulative material with a first end and an opposing second end;

at least two electrically conductive electrodes disposed in fixed longitudinal relation with at least a part thereof encased by the insulative material;

a plug formed at the second end of the body for connecting a meter to the body;

means for receiving a fluid sample;

means for detecting when a sufficient amount of fluid sample has been received selected from the group consisting of(a) an electrical indication and (b) a visual indication; and, one or more substances deposited on at least one of the electrodes to react with the fluid sample to produce electrochemical changes correlative to the concentration of an analyte in the sample.

7. An electrochemical device for cooperating with a meter to measure changes in electrochemical properties of a fluid sample as a result of chemical or enzymatic reactions comprising:

a unitary single piece body of insulative material with a first end and an opposing second end;

at least two electrically conductive electrodes disposed in fixed longitudinal relation with at least a part thereof encased by the insulative material;

means for connecting a meter to the body;

a capillary inlet molded into the first end for drawing the fluid sample into the body upon contact with the sample;

means for detecting when a sufficient amount of fluid sample has been received selected from the group consisting of (a) an electrical indication and (b) a visual indication; and, one or more substances deposited on at least one of the electrodes to react with the fluid sample to produce electrochemical changes correlative to the concentration of an analyte in the sample.

8. The electro chemical device of claim 7 further comprising a reaction zone formed in the body in communication with the capillary inlet.

9. The electrochemical device of claim 8 wherein the reaction zone is a channel containing at least a portion of each of the electrodes for analyzing the fluid sample drawn therein.

10. The electrochemical device of claim 9 wherein the means for detecting when a sufficient amount of fluid sample has been received includes a depressurization vent formed in the body in communication with the reaction zone.

11. The electrochemical device of claim 9 wherein the means for detecting when a sufficient amount of fluid sample has been received includes a sample fill vent in the body in communication with the reaction zone for filling with sample fluid and allowing for fill detection to be made visually.

12. The electrochemical device of claim 9 having an end cap pivotably attached to the body near the first end, the end cap having a sample fill vent that when the end cap is attached to the body, the sample fill vent substantially aligns with at least one of the electrodes.

13. The electrochemical device of claim 9 wherein the reaction zone lies in the bottom portion of the device.

14. The electrochemical device of claim 8 wherein the at least two electrodes terminate in the reaction zone, the reaction zone having a vent for relieving pressure.

15. An electrochemical device for cooperating with a meter to measure changes in electrochemical properties of a fluid sample as a result of chemical or enzymatic reactions, comprising:

a unitary single piece body of insulative material with a first end and an opposing second end;

at least two electrically conductive wires disposed in fixed longitudinal relation with a part thereof encased by the insulative material;

means for connecting a meter to the body;

means for receiving a fluid sample;

means for detecting when a sufficient amount of fluid sample has been received selected from the group consisting of (a) an electrical indication and (b) a visual indication; and one or more substances deposited on at least one of the conductive wires to react with the fluid sample to produce electrochemical changes correlative to the concentration of an analyte in the sample.

16. The electrochemical device of claim 15 wherein at least one wire is coated with a conductive material different then the composition of the wire.

17. An electrochemical device for cooperating with a meter to measure changes in electrochemical properties of a fluid sample as a insult of chemical or enzymatic reactions, comprising:

a unitary single piece body of insulative material with a first end and an opposing second end;

at least two electrically conductive electrodes formed from a conductive plate disposed in fixed longitudinal relation with a part thereof encased by the insulative material;

means for connecting a meter to the body;

means for receiving a fluid sample;

means for detecting when a sufficient amount of fluid sample has been received selected from the group consisting of (a) an electrical indication and (b) a visual indication; and, one or more substances deposited on at least one of the electrodes to react with the fluid sample to produce electrochemical changes correlative to the concentration of an analyte in the sample.

18. An electrochemical device for cooperating with a meter to measure changes in electrochemical properties of a fluid sample as a result of chemical or enzymatic reactions, comprising:

a unitary single piece body of insulative material with a first end and an opposing second end;

at least two electrically conductive electrodes disposed in fixed longitudinal relation with a part thereof encased by the insulative material;

means for connecting a meter to the body;

means for receiving a fluid sample;

means for detecting when a sufficient amount of fluid sample has been received selected from the group consisting of (a) an electrical indication and (b) a visual indication; and, one or more substances deposited on at least one of the electrodes to react with the fluid sample to produce electrochemical changes correlative to the concentration of an analyte in the sample, the substance including a coating on at least one electrode with at least one of a reagent and an enzyme.

19. An electrochemical device for cooperating with a meter to measure changes in electrochemical properties of a fluid sample as a result of chemical or enzymatic reactions, comprising:

a body of insulative material with a first end and an opposing second end;

at least two electrically conductive electrodes disposed in fixed longitudinal relation in the insulative material;

means for connecting a meter to the body;

means for receiving a fluid sample;

means for detecting when a sufficient amount of fluid sample has been received selected from the group consisting of (a) an electrical indication and (b) a visual indication; and, an enzyme on an outer surface of one of the electrodes and one of an enzyme-antibody conjugate and an enzyme-analyte conjugate is on another of the electrodes.

20. The electrochemical device of claim 19 wherein an electron mediator is on one or more of the electrodes.

21. An electrochemical device for cooperating with an electronic meter capable of measuring the electrochemical properties in a fluid sample resulting from chemical or enzymatic reaction, comprising:

a body of insulative material with a first end and a second end;

three electrically conductive electrodes spaced apart in fixed longitudinal relation to each other, housed in the body, the body including an electrode encasing unit and an end cap attached to one another with each being made of molded plastic;

a plug for connecting a meter to the body;

means for receiving a fluid sample in the body; and, means for detecting when a sufficient amount of fluid sample has been received for analysis selected from the group consisting of (a) an electrical indication and (b) a visual indication.

22. An electrochemical device for cooperating with an electronic meter capable of measuring the electrochemical properties in a fluid sample resulting from chemical or enzymatic reaction, comprising:

a unitary single piece body of insulative material with a first end and a second end;

three electrically conductive electrodes spaced apart in fixed longitudinal relation to each other with a part thereof encased by the body;

a plug for connecting a meter to the body;

a capillary inlet for drawing the fluid sample into the body upon contact with the fluid sample; and, means for detecting when a sufficient amount of fluid sample has been received for analysis selected from the group consisting of (a) an electrical indication and (b) a visual indication.

23. The electrochemical device of claim 22 further having a hinge constructed in the body permitting the pivoting and connecting of a portion of the body onto itself; and at least one energy director ridge formed in the body on at least one side of the hinge, such that securely affixing the energy director ridge to the body opposite side of hinge forms a reaction zone.

24. The electrochemical device of claim 23 further comprising one or more substances an one or more electrodes for reacting with the fluid sample to produce electrochemical changes measurable by the electrodes.

25. The electrochemical device of claim 23 wherein the one or more substances is a coating on at least one electrode with at least one of a reagent and an enzyme.

26. The electrochemical device of claim 23 wherein an enzyme is on the outer surface of one of the electrodes.

27. The electrochemical device of claim 26 wherein an electron mediator is on the outer surface of one or more of the electrodes.

28. The electrochemical device of claim 22 having a hinge constructed in the body permitting the pivoting and connecting of a portion of the body onto itself; and at least one protuberance formed in the body on one side of the hinge to mate with at least one recessed surface in the body on the other side of the hinge.

29. The electrochemical device of claim 28 further comprising one or more substances on one or more electrodes for reacting with the fluid sample to produce electrochemical changes measurable by the electrodes.

30. The electrochemical device of claim 28 wherein the one or more substances is a coating on at least one electrode with at least one of a reagent and an enzyme.

31. The electrochemical device of claim 28 wherein an enzyme is on the outer surface of one of the electrodes.

32. The electrochemical device of claim 31 wherein an electron mediator is on the outer surface of one or more of the electrodes.

33. An electrochemical device for cooperating with an electronic meter capable of measuring the electrochemical properties in a fluid sample resulting from chemical or enzymatic reaction, comprising:

a body of insulative material with a first end and a second end;

three electrically conductive electrodes spaced apart in fixed longitudinal relation to each other, housed in the body;

a plug for connecting a meter to the body;

means for receiving a fluid sample in the body; and, a cavity forming a reaction zone in the body, the reaction zone having at least a portion of each electrode exposed therein for reacting with the fluid sample, such that sample drawn into the reaction zone contacts the exposed portion of at least one of the electrodes and activates the meter to indicate sufficient fill.

34. The electrochemical device of claim 33 wherein the reaction zone is in fluid communication with a capillary inlet.

35. An electrochemical device for cooperating with an electronic meter capable of measuring the electrochemical properties in a fluid sample resulting from chemical or enzymatic reaction, comprising:

a unitary single piece body of insulative material with a first end and a second end;

three electrically conductive electrodes spaced apart in fixed longitudinal relation to each other with a part thereof encased by the body, the electrodes being one of isolated conductive wires and wires associated with a conductive plate;

a plug for connecting a meter to the body;

means for receiving a fluid sample in the body; and, means for detecting when a sufficient amount of fluid sample has been received for analysis selected from the group consisting of (a) an electrical indication and (b) a visual indication.

36. An electrochemical device for measuring the concentration of an analyte by cooperating with an electronic meter capable of measuring the electro chemical properties of a fluid sample resulting from chemical or enzymatic reaction, comprising:

a unitary, single molded plastic body with two opposing ends;

at least two spaced apart electrically conductive electrodes with a part thereof encased by the molded body;

a plug formed at one end of the body exposing the electrodes outside the body for connecting the meter to the body;

an inlet molded into the other end of the body defining a capillary for drawing the fluid sample into the body upon contact with the fluid sample;

a reaction zone in communication with the capillary, there action zone having an interior surface and at least a portion of each electrode exposed therein for reacting with the fluid sample, such that sample drawn into the reaction zone contacts the exposed portion of at least one electrode and activates the meter to indicate sufficient fill; and one or more substances on at least one of the interior surface of the reaction zone and at least one of the electrodes such that the one or more substances react with the fluid sample to produce electrochemical changes measurable by the meter.

37. The electrochemical device of claim 36 wherein the reaction zone has a volume defined by the shape of at least one of the body and an end cap securely affixable to the body.

38. The electrochemical device of claim 36 wherein the electrodes are embedded in the body as one of isolated conductive wires and a composite conductive plate.

39. The electrochemical device of claim 36 having a hinge constructed in the body permitting the pivoting and connecting of a portion of the body onto itself; and at least one protuberance formed in the body on one side of the hinge to mate with at least one recessed surface in the body on the other side of the hinge to form the reaction zone.

40. The electrochemical device of claim 36 having a hinge constructed in the body permitting the pivoting and connecting of a portion of the body onto itself; and at least one energy director ridge formed in the body on one side of the hinge and securely affixable to the body on the opposite side of the hinge to form the reaction zone.

41. The electrochemical device of claim 36 wherein the one or more substances comprises a coating having at least an enzyme.

42. The electrochemical device of claim 41 wherein the coating includes one of an enzyme-antibody conjugate and an enzyme-analyte conjugate.

43. The electrochemical device of claim 41 wherein the coating includes an electron mediator.

44. A sensor comprising:

a body having an end for cooperating with a meter and an end for receiving a fluid sample;

a plurality of electrically conductive leads with a part thereof around which a portion of the body has been molded so as to be encased by the body and having at least one lead extending into the end for receiving the fluid sample;

a cavity in the body to detect sufficiency of sample quantity; and, an enzyme deposited on at least one of the leads.

45. The sensor of claim 44 wherein the body is formed from a moldable material and made in a mold.

46. The sensor of claim 44 wherein the leads are at least partially exposed at the end for cooperating with the meter.

47. The sensor of claim 44 wherein the cavity is formed in the lower portion of the body and communicates with the end for receiving the fluid sample, such that the fluid sample contacts a portion of the leads to produce a measurable change in the fluid.

48. The sensor of claim 44 wherein at least one of the leads is a wire conductor.

49. The sensor of claim 44 wherein at least one of the leads is a stamped conductive metal member.

50. The sensor of claim 49 wherein the stamped conductive metal member is coated with another electrically conductive material.

51. The sensor of claim 44 wherein at least two of the plurality of the leads include different metals.

52. The sensor of claim 44 wherein the body has a plurality of guides molded therein to prevent the leads from moving within the body.

53. The sensor of claim 44 wherein the end for receiving a fluid sample includes a capillary inlet.

54. The sensor of claim 53 wherein the capillary inlet is in communication with the cavity for detecting sufficient fill.

55. A sensor comprising:

an injection molded plastic body having a meter-attachment end and a fluid sample receiving cavity;

a plurality of electrically conductive leads with a part thereof encased by the body and with at least one lead extending from the attachment end to the fluid sample receiving cavity;

a plurality of vents communicating with the fluid sample receiving cavity for detecting the sufficiency of the amount of the fluid sample received; and, an enzyme disposed within the fluid sample receiving cavity.

56. The sensor of claim 55 wherein the cavity and the leads are in a bottom portion of the sensor, such that the sample contacts the edges of the leads to produce a measurable electrical change in the fluid.

57. The sensor of claim 55 wherein the leads are at least partially expose at the attachment end of the molded body.

58. The sensor of claim 55 wherein at least one of the leads is a stamped conductive metal member.

59. The sensor of claim 55 wherein the stamped conductive metal member is coated with an electrically conductive material different than the composition of the lead.

60. The sensor of claim 55 wherein the body has a plurality of guides molded therein to hold and maintain the leads within the body.

61. The sensor of claim 55 wherein the enzyme is disposed on at least one of the leads.

62. A sensor for analyzing a fluid sample comprising:

an injection molded body having an attachment end and a sample receiving zone;

a plurality of electrically conductive leads with at least a part thereof encased by the body, the leads extending in substantial alignment between the two ends, at least one of the leads extending into the sample receiving zone and the body having a plurality of guides molded therein with at least one of the guides abutting against at least one of the leads;

a substance deposited within the sample receiving zone for analyzing the fluid sample; and, a vent communicating with the sample receiving zone for determining adequate sample fill.

* * * * *

UNITED STATES PATENT AND TRADEMARK OFFICE
CERTIFICATE OF CORRECTION

PATENT NO. : 6,572,745 B2  Page 1 of 1
DATED : June 3, 2003
INVENTOR(S) : Craig Rappin, Kiamars Hajizadeh, and Kelly Mills It is certified that error appears in the above-identified patent and that said Letters Patent is hereby corrected as shown below:

Column 16,
Line 58, after the word "zone" insert -- in the body. --
Line 60, delete "last" and insert -- least -- therefor.

Column 17,
Line 19, after "reactions" insert -- , --.
Line 37, delete the space between "electro" and "chemical".
Lines 59-63, the text of claim 13 should be numbered -- 14 -- and the text of claim 14 should be numbered -- 13 --.

Column 18,
Line 12, after "and" insert -- , --.
Line 22, delete "insult" and insert -- result -- therefor.

Column 19,
Line 57, delete "an" and insert -- an -- therefor.

Column 21,
Line 4, delete "there" and insert -- the -- therefor.

Signed and Sealed this

Twenty-second Day of June, 2004

JON W. DUDAS
*Acting Director of the United States Patent and Trademark Office*